United States Patent [19]

Chiang

[11] Patent Number: 4,590,792
[45] Date of Patent: May 27, 1986

[54] MICROANALYSIS PARTICLE SAMPLER

[76] Inventor: William W. Chiang, 305 W. Orange Grove Ave., Sierra Madre, Calif. 91024

[21] Appl. No.: 668,006

[22] Filed: Nov. 5, 1984

[51] Int. Cl.[4] .............................................. G01N 15/02
[52] U.S. Cl. ...................................... 73/28; 250/440.1
[58] Field of Search ............. 73/28, 432 PS; 250/311, 250/440.1, 306, 307; 55/270

[56] References Cited

U.S. PATENT DOCUMENTS

| 3,224,434 | 12/1965 | Molomut et al. | 73/28 |
| 3,972,226 | 8/1976 | Rountree et al. | 73/28 |
| 3,983,743 | 10/1976 | Olin et al. | 73/28 |
| 4,301,371 | 11/1981 | Lieb | 250/311 |

OTHER PUBLICATIONS

C. J. Peat, "A Modified Specimen Stub for the Scanning Electron Microscope", Journal of Microscopy, vol. 101 Pt. 3, pp. 323-327, Aug. 1974.

Primary Examiner—Stephen A. Kreitman
Attorney, Agent, or Firm—William W. Haefliger

[57] ABSTRACT

Apparatus of the invention enables gas entrained particulate collection and transfer of collected particulate into position for scanning by a scanning electron microscope; and it comprises:

(a) structure forming a cavity and including a nozzle having an orifice for directing flow of gas and particulates entrained therein toward the cavity, (b) and a holder mounted in the cavity in association with such structure and having an electrically conductive surface facing toward the orifice in the path of flow and normal to the path of flow from the orifice so that particulates collect on the holder proximate said surface, (c) the holder being sized and adapted for use in the scanning electron microscope whereby the holder may be directly transferred to that microscope for electron beam scanning of the in situ collected particulate.

21 Claims, 14 Drawing Figures

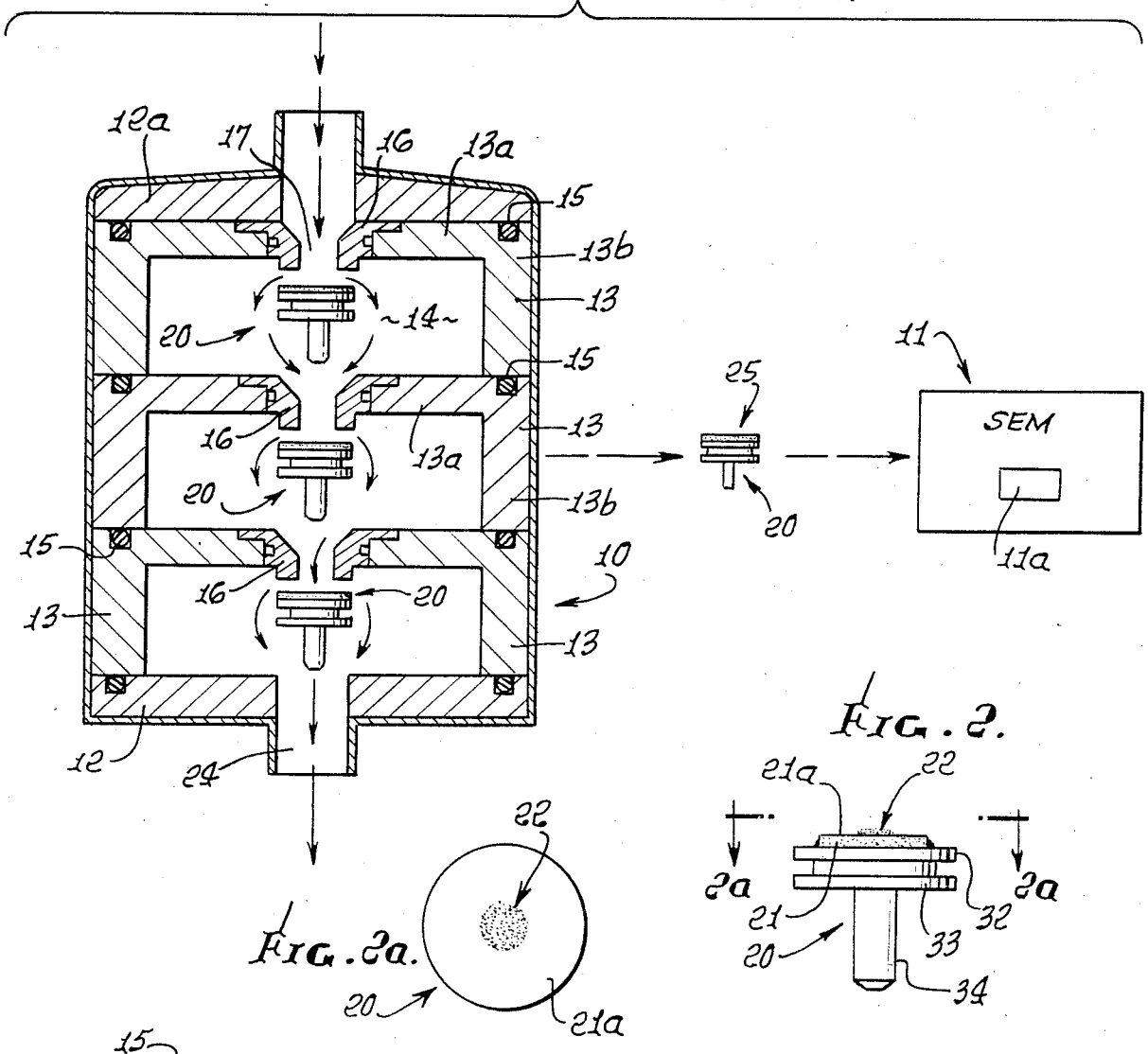
Fig. 1.
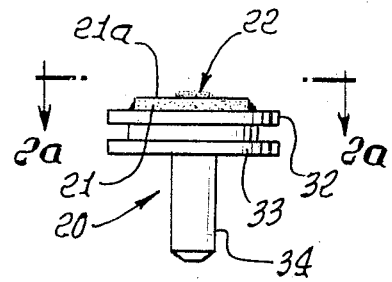
Fig. 2.
Fig. 2a.
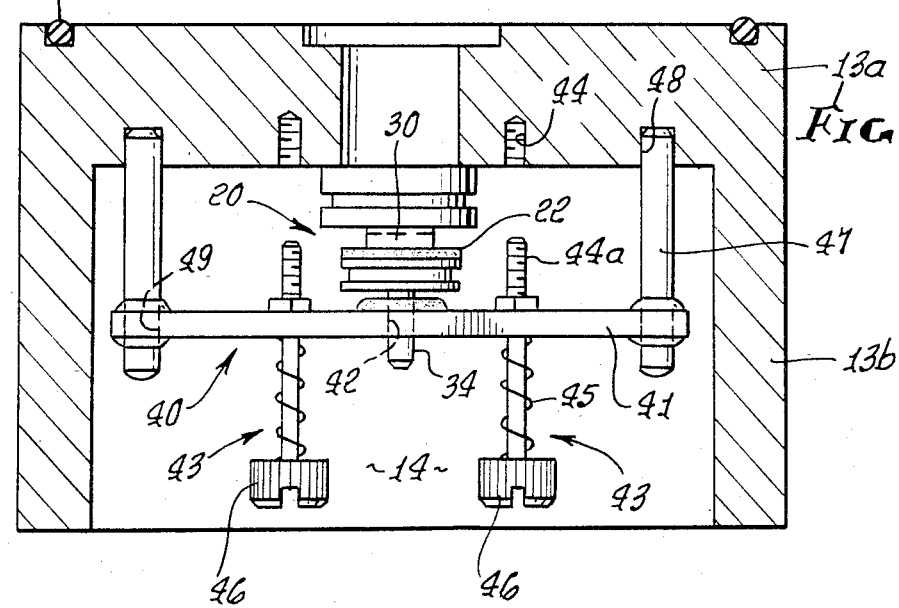
Fig. 3.

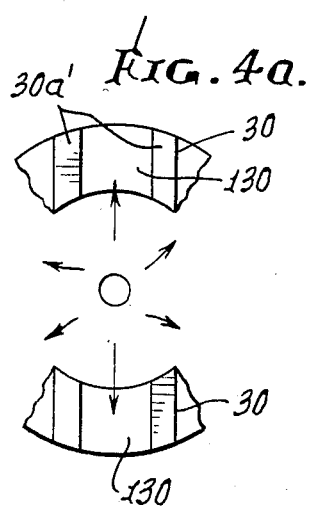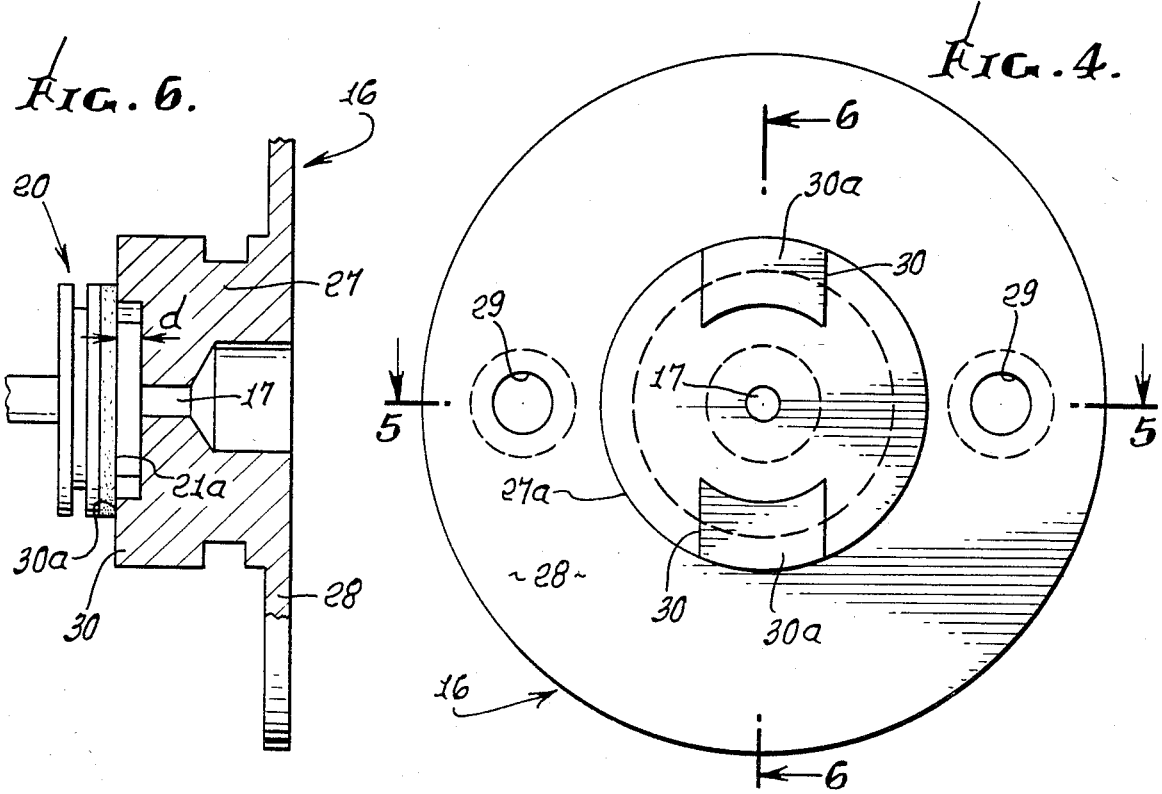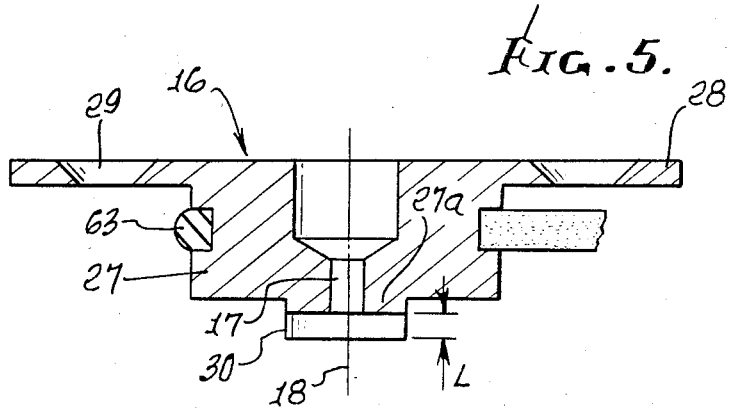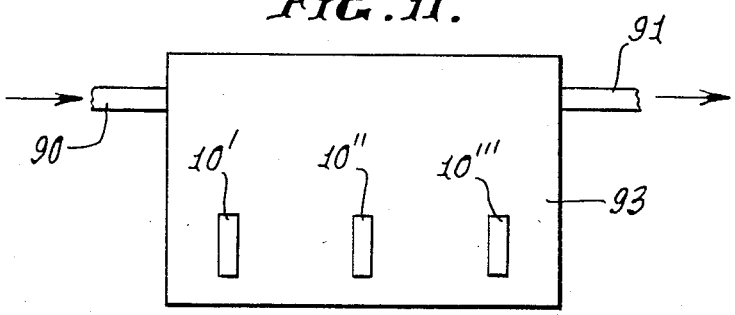

MICROANALYSIS PARTICLE SAMPLER

BACKGROUND OF THE INVENTION

This invention relates generally to particle analysis instrumentation and techniques, and more particularly concerns apparatus and method for collection of particle samples in such manner as to facilitate analysis in a scanning electron microscope (SEM), eliminating handling between sampler and SEM.

There is a continuing need to collect and identify small particles which, for example, are dispersed or entrained in gases, such as air. By way of illustration, manufacturers of semiconductors, pharmaceuticals, and other high precision products are very concerned about the presence of airborne microcontaminants in their manufacturing facilites. The presence of airborne particulate contaminants can cause serious drops in production yields and increase product failures. They therefore invest heavily in clean rooms to provide highly filtered air and a clean environment for their manufacturing plants. Very small respirable airborne microcontaminants are also of serious concern to researchers in environmental health.

However, because of filter failures, or the presence of personnel, or for a number of other reasons, the concentration of airborne particles can or does increase to unacceptable levels. When this happens, it is very important to know what the particles are and where they came from.

At the present time, the routine monitoring of the presence of airborne particles is carried out through the use of optical particle counters. This type of instrument utilizes light scattering principles to report the number of particles present per unit volume, for particles larger than 0.3 microns. It does not retain the samples being measured; they simply pass through the instruments.

To find out what the particles are requires the collection of samples of the particles and then their identification through modern microanalysis techniques, i.e., Scanning Electron Microscopy (SEM) and X-ray Energy Spectroscopy (XES), such as Energy Dispensive X-ray Analysis (EDXRA). Because the particles are as small as 0.1 microns or less, the high magnification capabilities of the scanning electron microscope are required. Optical microscopes are not good enough.

The high magnification and three dimensional capabilities of the scanning electron microscope provide detailed information on the shape, size, texture, topology, and the structure of individual particles. An electron microscope with an X-ray detector attachment gives it the added capability of EDXRA to provide elemental composition information on the particle sample as well. SEM and EDXRA are established techniques for microanalysis of very small particles.

In an electron microscope an electron beam performs the function of a light beam in an optical microscope. When a particle specimen is being examined, it is the electron beam that bombards the particle. If the particle is nonconductive, a charge build-up on the particle caused by the electron beam bombardment must be minimized. To accomplish this, the sample is coated with a thin layer of carbon which is conductive, or with gold.

Accordingly, electron microscopists think in terms of physically transferring particles from non-conductive substrates and mounting them on conductive substrates which are integral parts of conductive holders which can fit directly into a scanning electron microscope (S.E.M.). If, for example, the particles are collected on a filter, the microscopist must either cut a piece of the filter paper with particle sample on it and mount it on the conductive holder substrate, and then coat it with carbon, etc., or he must remove and transfer the particle specimens individually.

All these procedures are very time consuming and fraught with errors and the introduction of contamination. For example, if one can mount a clean 1 $\mu$m ($10^{-12}$ g) particle on a polished beryllium plate, one can look at it with the scanning electron microscope and analyze it quantitatively with the electron or ion microprobe. The transmission electron microscope will provide a good look at $10^{-15}$ g (0.1 $\mu$m$^3$) particles, as well as a good electron diffraction pattern. The ion microprobe will detect $10^{-18}$ g of any element in femtogram ($10^{-15}$ g) particles.

Most samples can be examined directly without fractionation. If, however, the particle of interest is embedded in a matrix and if it must be removed for identification either microscopically or by other techniques, another major problem is introduced. The particles must be isolated, or separated into distinct groups, at least in the field of view of the microscope. Often they must be actually picked out physically.

Manipulation of tiny single particles is not easy. It requires a great deal of skill on the part of the microscopist and fine tools. A careful microscopist with very steady hands can, however, with some practice, "pick up and deliver" particles smaller than one micrometer in diameter. The modus operandi for a particular particle depends on where it is, that is, on the medium that surrounds or supports it. In general, it may be lying on or embedded in paper, glass, metal, ceramic, paint, polymer film or any other material. Or it may be mixed in a liquid medium (water, glycerin, etc.) on a microscope slide, in some other refractive index medium or in the adhesive layer of transparent tape. In any case, the microscopist must spend time and exercise great care in extraction the particle samples for mounting on a conducting substrate and mount before analysis in an S.E.M.

Very few experts in X-ray diffraction, electron microscopy or microprobe analysis are adept at handling single particles near the limits of sensitivity of their instruments. The techniques require a clean atmosphere, steady hands, practice and very fine needles. Such procedures are time consuming and require adherence to the following:

(1) never take one's eyes off the particle during a manupulative operation;
(2) remove the particle from the needle only by "washing" it off into a micro drop of liquid to which the particle will adhere or in which the adhesive holding the particle to the needle will dissolve;
(3) to be picked up, a particle must be loose, be touched with a liquied film on a needle more viscous and tacky than its environment, or be picked using a freezing needle to pick up a small frozen volume of the liquid film with the occluded particle. Excess liquid around a particle is removed in different ways, depending on the fluidity. If it is quite fluid, the excess liquid can usually be soaked into a small triangle of thin lens tissue while one keeps a close watch on the particle with the microscope. If the liquid is very viscous (e.g. Canada balsam or Aroclor), the same operation is carried out, but after dilution with benzene. Because each situation is unique, patience, ingenuity and self-confidence are the essential ingredients for success.

From the foregoing, it is clear that a need exists for simplification of particle collecting and handling techniques, particularly as respects collected particle transfer to an SEM.

SUMMARY OF THE INVENTION

It is a major object of the invention to provide instrumentation and method to meet the above need, and to overcome the above difficulties and problems.

Basically, the invention stems from the insight, previously unrealized, that gas or air samples in which particulate is entrained can be drawn through an impactor, such as a multi-stage cascade impactor, and particle samples can be collected on conductive, low X-ray background substrates, which can be removed and inserted directly into a scanning electron microscope. The samples can then be analyzed as they were collected. This eliminates particle handling between the sampler and the SEM, avoiding possible contamination of the samples and making diagnosis of the causes of contamination problems much faster. The cascade impactor segregates submicron particles from larger ones during sampling, making identification of particles of different size groups and species easier and more accurate.

As respect the apparatus of the invention, they are typically embodied in the provision of impactor structure forming a cavity and including a nozzle having an orifice of a small number of orifices, for directing flow of the gas and particulates toward the cavity; and (x) a holder mounted, or to be mounted, in the cavity in association with said structure and having an electrically conductive surface integral to or mounted on a conductive stem facing toward said orifice or orifices in the path of flow from the orifice and normal to it so that particulates collect on the holder proximate said surface, (y) the holder sized and adapted for use in the scanning electron microscope, whereby the holder may be directly transferred to said microscope for electron beam scanning of said particulates.

The method of using such apparatus includes the steps:

(i) flowing said gas and entrained particulates through said nozzle and toward said holder surface,
(ii) collecting particualtes on said surface,
(iii) then demounting said holder from said structure and directly transferring the holder to a scanning electron microscope, and
(iv) operating the microscope to scan the particulates on the holder surface.

Further, and as will be seen, multiple of such structures (having disc or cup-shape, for example) may be arranged in a stack so that the gas flows in sequence through said nozzles and cavities, there being multiple of said holders, one positioned in each of said cavities as defined in (b) of claim 1. The holder surface typically consists of a substance selected from the group consisting of beryllium or carbon, these being low molecular weight materials, and the holder has a body consisting of an electrically conductive metal or metal alloy, and the holder body may include a stem, and a flange on the stem for mounting said surface; said surface is defined by a substrate of said substance. Said surface and holder body may also be of the same substance, made from a single piece of material.

In addition, a bracket may mount the holder, the bracket located in the cavity and removably attached to said structure which is cup-shaped; and the holder is typically positioned by the bracket so that at least one portion of said surface is retained in engagement with the nozzle, whereby said surface is accurately positioned normal to the airflow relative to the orifice. The bracket is advantageously removably mounted to the cup-shaped structure, as will be seen, so that multiple functions are provided, ease of removal of the bracket from the impactor disc and nozzle assembly; retention of the holder or "stub" collection surface at pre-selected spacing from the orifice as well as clamped against the nozzle; ease of removal of the holder or stub from the bracket; and relative rotation of the holder and nozzle to facilitate collection of particulates at multiple locations on the holder, greatly enhancing its utility vis-a-vis particle scanning by the SEM.

Another object of the invention is to provide a rotary drive system to achieve such relative rotation, as will appear.

These and other objects and advantages of the invention, as well as the details of an illustrative embodiment, will be more fully understood from the following specification and drawings, in which:

DRAWING DESCRIPTION

FIG. 1 is a schematic view in elevation of a particulate collection system employing the invention;

FIG. 2 is an enlarged elevation of a holder, as employed in FIG. 1;

FIG. 2a is a plan view on lines 2a–2c of FIG. 2;

FIG. 3 is an enlarged elevation showing mounting of a holder by a bracket connectible to cup-shaped structure;

FIG. 4 is an enlarged plan view of a nozzle as used in FIG. 1; and FIG. 4a is a modification;

FIG. 5 is a section taken on lines 5—5 of FIG. 4;

FIG. 6 is a section taken on lines 6—6 of FIG. 4;

FIG. 11 shows collectors in a room.

DETAILED DESCRIPTION

Figure 7:
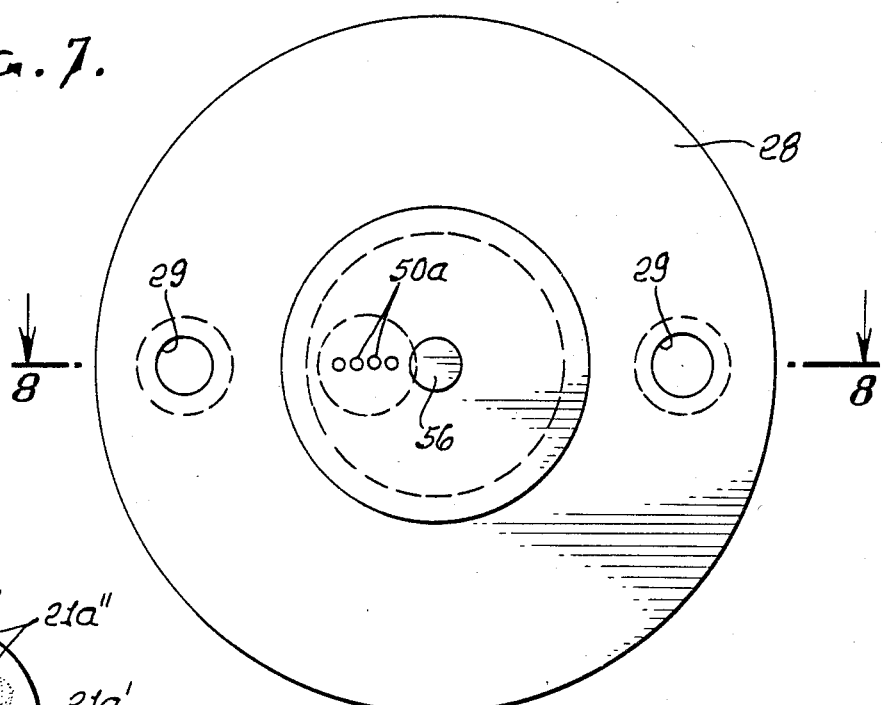
FIG. 7 is a view like FIG. 4, showing a modified nozzle.

Referring first to FIGS. 1, 2, 4, 5 and 6, apparatus 10 enables gas entrained particulate collection and transfer, as to an SEM 11, for electron beam scanning in the latter. Apparatus 10 includes structure forming a cavity, or cavities, and a nozzle (or nozzles) having an orifice for directing flow of gas and particulates entrained therein toward the cavity or cavities. In the example, the structure includes a base 12, a cap 12a, and one or more (typically 2–6) cup-shaped structures 13, each having a horizontal top wall or plate 13a and a skirt 13b, forming a cavity 14. O-ring seals are indicated at 15 to seal off the structures 13, one from another, and the cup and base, as shown. Further, each structure includes a nozzle indicated at 16, one form being shown in detail in FIGS. 4–6.

The nozzles has an orifice 17 directed axially vertically, to flow gas and entrained particulates downwardly toward the cavity 14 in the associated structure 13. In FIGS. 4–6, the orifice 17 is located at the center of the disk-like structure 13, and extends generally coaxially therewith (see axis 18).

A holder 20 is mounted in each cavity in association with the structure 13, and has an electrically conductive surface 21a, as for example on substrate 21, facing upwardly toward the orifice in the direct downward path of flow from the orifice, so that particulate 22 collects (see FIG. 2) on the holder proximate the orifice. A thin layer of sticky substance, such as grease or oil, is sometimes applied to the center portion of the collection surface to increase particulate adhesion, for very dry particles. Gas (such as air) impacts the surface 21a, and then flows laterally as indicated (see arrows), about the holder and downwardly in the cavity 14, and then toward and through the next orifice, etc., as shown. Successive orifices have smaller diameters or cross sections, so that smaller particulate collects on the successive holders; the smallest particulates for example collect on the third and lowest holders 20, as shown in FIG. 1. The air ultimately flows from the device via port 24.

After collection of particulates on the holders 20, they are directly transferred, as indicated schematically at 25, to the SEM 11, for electron beam scanning of the undisturbed particulates; and the holder (compatible in size, and shape with mounts 11a in the SEM) are subsequently re-usable after cleaning.

Note in FIGS. 4–6 that the nozzles have bodies 27 through which orifice 17 extends, centrally; and upper flange 28, via which the nozzles are attachable to plates 13a as via fasteners extending through openings 29. Bodies 27 have bottom bosses at 27a which define two lands 30. The lower surfaces 30a of the latter are engaged by spaced portion of the holder top surface (see FIG. 6) 21a, to precisely space or position surface 21a from the orifice (see dimension "d"), for optimum particulate collection.

The stub, being metal (such as aluminum) for electrical conductivity, in most cases, performs the electrical function of draining charge current from the substrate on top of it to the body of the SEM. Its mechanical configuration is dictated by the different makes of SEM. A 0.5 inch diameter stub having upper flanges 32 and 33 (see FIG. 2) with a ⅛ inch diameter stem 34 is the most common and fits a number of models of different SEM makes. It is adaptable to other mount requirements, easily, because it is one of the smallest.

When the stub is mounted as at 11a inside the specimen chamber of the SEM, it is on a turret or platform which can assume different angles with respect to the electron beam. It can also be rotated 360°.

Receptability of the holder inside the parficle sampler 10 is important, because it is the mechanical interface required between the collection substrate and the SEM specimen chamber. If it were not attached to the substrate as at assembly and mounted inside the sampler, and if the substrate (a thin 1/16 inch wafer, for example) were alone used for particle collection, it would have to be conductively mounted to the stub after sample collection. Once again, this is an extra step that should be avoided, because it is time consuming when many wafers are to be handled—they can easily get mixed up. Furthermore, the particulate samples on the wafers may become contaminated during this extra step.

Therefore, from the handling and avoidance of contamination points of view, even contending with conductive substrates is not desirable after sample collection. Storing a substrate-stub-assembly is much easier and more convenient for markings and applying labels for identification.

The stub configuration of FIG. 2 is representative, but could be in the form of a round cylinder with a threaded stud, or with a stem slightly larger than ⅛ inch (e.g. ⅜" diameter).

As respects the apparatus 10, when a few stages are arranged in tandem, the terms "cascade impactor" is used. Inertial impactor and cascade impactors are used mostly for size separation of airborne particles simulating the function of the human lungs, or the respiratory tract. Most efforts in impactor design are in accurate size-cuts, increases in collection efficiencies. The primary features are:

1. size separate particles in close size steps, accurately,
2. collect sufficient amount of particles so that they can be weighed on a microbalance to determine relative concentrations.

The main features of design for these conventional impactors are:

3. high flow rates—1CFM (28.3 liters/min.) or higher and seldom less than 0.35 CFM (10 liters/min.),
4. each impactor size has multiple jets; (Andersen impactor, the most popular, has 200–400 jets per stage),
5. requires high vacuum capacity pump.

The type of impactor system used herein is just the opposite, and is characterized typically by:

1. Use of a low flow rate: from 0.25 liters/min. (0.008 CFM) to 2 liters/min. (0.071 CFM). The maximum flow rate is about 5 liters/min. (0.177 CFM).
2. With such low flow rates, single jets can be used in the impactor nozzle to separate particles down to 0.3 microns. For particles less than 0.3, down to 0.05 microns, two or four very small jets are used.
3. The low flow rate allows the use of jets with small diameters and pressure drops of up to 300 nm of mercury (Hg) across the jets can be induced. The larger single jet is typically not more than 0.1 inch in diameter. The smaller multi-jet diameters are as small as 0.0047 inch diameter. This allows one to impact the samples onto the substrate within a small circle, not larger than 0.1 inch diameter. See FIG. 2a.
4. The low flow rate enables one to separate particles less than 0.3 microns, down to 0.05 microns. This is not possible with high flow rates, because the pump requirements are unmanageable.
5. The low rate feature enables one to use a small pump. This makes the whole instrument small and portable.

For pollutant aerosols, the distribution of a particular chemical species with respect to particle size is important in the evaluation of health effects and transport behavior. Cascade impactors commonly used for the size segregation of aerosols for chemical analysis are generally capable of collecting particles as small as 0.5 μm. However, a large percentage of the urban aerosol is too small to be size fractionated by these impactors. For example, impactor measurements of urban sulfate show the mass median diameter is typically between 0.4 and 0.6 μm. Thirty to seventy percent of the sulfate aerosol passes through the impactor to be collected on the after filter. For characterizing particulate emissions from combustion sources, small particles are of interest not only because of their high concentration, but also because certain trace elements concentrate in the submicron aerosol. Thus, it is important to be able to size segregate aerosol for chemical analysis below 0.5 μm, for example between 0.5 and 0.3 μm.

One way to obtain size fractionated samples of these small aerosols is to operate an impactor at reduced pressure. At low pressures the means free path in the air is comparable to the diameter of the aerosol, reducing the drag on the particles and thus enabling their collection. Multijet low-pressure impactors have been built, capable of size segregation to 0.05 μm.

An inherent difficulty with reduced pressure impactors, especially for field work, is the pumping requirement necessary to obtain a low pressure at a reasonably large flow rate. For example, to operate at a mass flow of 10 L (STP) per minute at a pressure of 20 mm Hg absolute would require a pump with a 380-L/min displacement, which weights 200 lb.

It is advantageous to have an impactor compatible with the most sensitive analytical techniques so that a lower sample rate may be used. Of interest is the technique of flash volatilization and subsequent gas-phase detection. By this method a sample that is concentrated within an area of 20 mm$^2$ can be analyzed for sulfur containing compounds or nitrate. The sensitivity of these methods results from the ability to analyze the sample directly, without the extraction that would be required with a multijet impactor sample. With a single jet impactor a flow of 1 L/min is sufficient to be able to obtain urban aerosol sulfur or nitrate size distribution in a 30–120 min sample period.

Referring to FIGS. 1 and 3, a bracket 40 is shown as mounting the holder or stub 20, the bracket removably received or located in the cavity 14, and removably attached to the disk-like structure 13. The bracket may advantageously include a cross-piece or arm 41 extending laterally and mounting the holder, as via a hole 42 in the bracket receiving the stem 34. Fasteners 43 are proved at generally opposite sides of the holder for removably attachment to the disk plate 13a, as via threaded openings 44 in the latter to threadably receive the threaded fastener shanks 44a. Springs 45 between the fastener heads 46 and cross-piece yieldably urge the latter and holder 20 toward nozzle lands 30. Guide rods 47 on the cross-piece are receivable in guided openings 48, and guide movement of the cross-arm toward the nozzle (the arm may contain openings 49 to pass the guide rods).

It will be noted that the holder is positioned by the bracket so that at least one portion of the surface 21a is yieldably retained (as by springs 45) in slidable engagement with the nozzle (as for example land surfaces 30a engaging laterally spaced portion of surface 21a), whereby the collection surface 21a is accurately positioned (as by precise gap "d") relative to the orifice. Also, the collection surface extending between land surface 30a is precisely aligned with the orifice, to receive particulate impact.

Figure 8A:
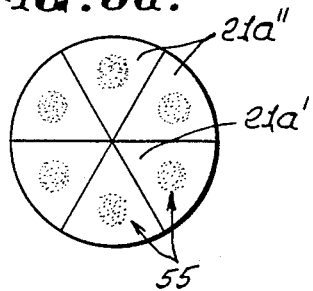
FIG. 8a is a plan view of modified holder collection surface.
Figure 8:
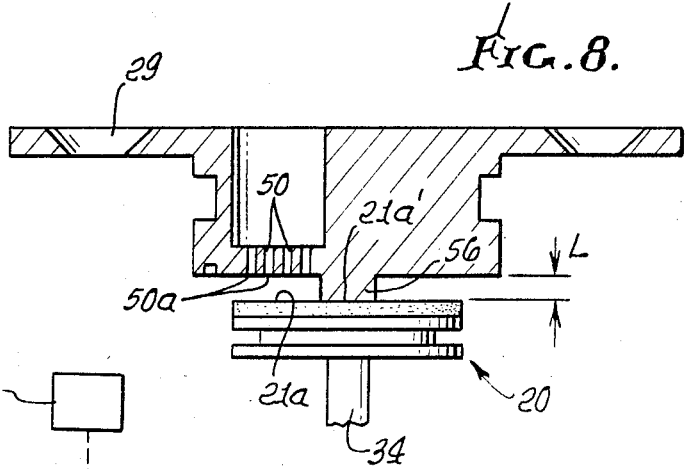
FIG. 8 is a section on lines 8—8 of FIG. 7, and showing a holder positioned by the nozzle.

Turning now to FIGS. 7 and 8, the modified orifices 50 have outlets 50a offset laterally relative to a medial or center portion 21a' of the holder surface 21a, so that multiple surface portions 21a' of the holder or stub may be brought into successive alignment with the orifice, and particulate may be collected in groups 55 on the respective surface portions. Note that the holder medial surface 21a' engages central land 56 of the nozzle, in this embodiment.

If desired, the holder may be rotated relative to cross-piece 41, to successively present surface extents 21a'' beneath orifice 50.

Figure 9:
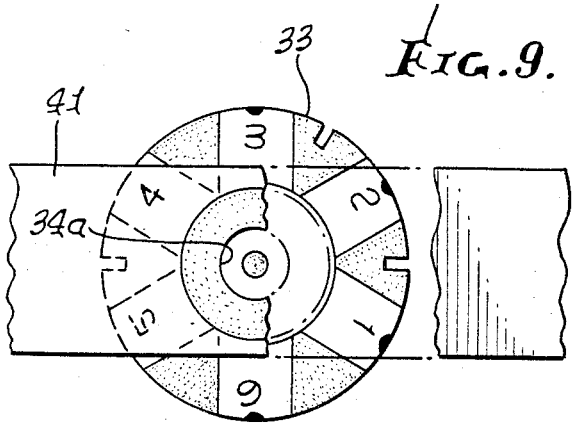
FIG. 9 is an enlarged fragmentary view of a bracket and holder, which is rotatable between successive positions.

FIG. 9 shows the holder stem 34 frictionally retained in opening 34a in the cross-piece so that when the holder is rotated, it remains in selected positions. Markings 1–6 on the underside of flange 33 indicate the positions of the surface extents 21a' relative to orifice 50.

Figure 10:
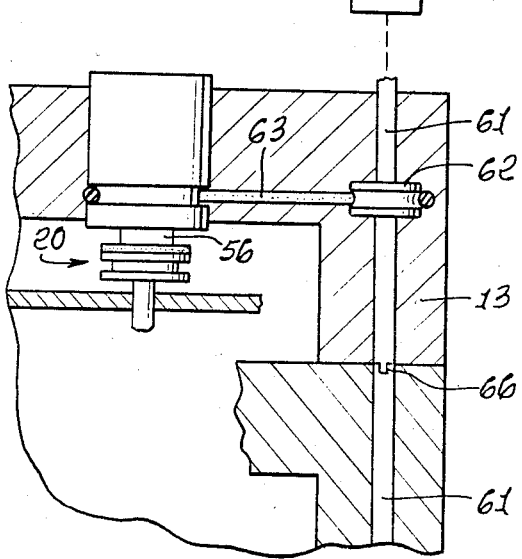
FIG. 10 is a schematic view of a drive system to relatively rotate multiple nozzles relative to multiple holders.

Alternatively, the nozzle may be rotated relative to the holder to each of a selected number of positions to bring it successively into alignment with holder surface portions 21a''. See for example the drive system in FIG. 10 that includes step-motor 60, shafts 61 driven by the motor, hubs 62 on the shafts, and drive belts 63 extending around the hubs and around the nozzles (see also FIG. 5). The nozzles have rotatably slidably interfit with top plates 13a, and their lands 56 slide on the top surfaces of the holders. Shafts 61 in the units 13 have ends that intercouple as at 66 when units 13 are assembled in stacked relation.

In FIG. 4a, the modified lands 30 are radially channeled at 130, to radially pass the flow from orifice 17 in two additional channels, thereby increasing the transverse flow direction across the stub surface. Four feet 30a' are thereby created, to engage surface 21a.

FIG. 11 shows multiple units 10 in a room 93 to sample air borne particulates at different points 10', 10'', and 10''', air entering and leaving the room at 90 and 91.

I claim:

1. In apparatus enabling gas entrained particulate collection and transfer of collected particulate into position for analysis by a scanning electron microscope, the improvement comprising
   (a) structure forming a cavity and including a nozzle having an orifice for directing flow of said gas and particulates entrained therein toward the cavity, said orifice having a cross dimension less than about 0.1 inch,
   (b) and a holder mounted in the cavity in association with said structure and having an electrically conductive surface facing toward said orifice in the path of flow and normal to the path of flow from the orifice so that particulates collect on the holder proximate said surface,
   (c) the holder sized and adapted for use in the scanning electron microscope whereby the holder may be directly transferred to said microscope for electron beam scanning of said particulate,
   (d) the holder surface consisting of a low molecular weight substance, and the holder having a body consisting of electrically conductive metal or metal alloy.

2. The apparatus of claim 1 wherein there are multiple of said structures arranged in a stack so that the gas flows in sequence through said nozzles and cavities, there being multiple of said holders, one positioned in each of said cavities as defined in (b) of claim 1.

3. The apparatus of claim 1 wherein said orifice has an outlet offset relative to a medial portion of the holder surface so that multiple surface portions of the holder spaced about said medial portion may be brought into successive alignment with said orifice and particulates may be collected in groups on said respective surface portions.

4. The apparatus of claim 3 wherein the holder and nozzle are carried to be relatively rotatable to bring said multiple surface portions of the holder into successive alignment with said orifice, as defined in claim 3.

5. The apparatus of claim 4 wherein the holder has a central stem defining a longitudinal axis directed toward the nozzle, and relative to which said orifice is laterally offset.

6. The apparatus of claim 4 including means to relatively rotate the nozzle and holder, as defined.

7. The apparatus of claim 6 wherein there are multiple of said structures arranged in a stack so that the gas flows in sequence through said nozzles and cavities, there being multiple of said holders, one positioned in each of said cavities as defined in (b) of claim 1.

8. Multiple collector units as defined in claim 1, in a room.

9. In apparatus enabling gas entrained particulate collection and transfer of collected particulate into position for analysis by a scanning electron microscope, the improvement comprising (a) structure forming a cavity and including a nozzle having an orifice for directing flow of said gas and particulates entrained therein toward the cavity, (b) and a holder mounted in the cavity in association with said structure and having an electrically conductive surface facing toward said orifice in the path of flow and normal to the path of flow from the orifice so that particulates collect on the holder proximate said surface, (c) the holder sized and adapted for use in the scanning electron microscope whereby the holder may be directly transferred to said microscope for electron beam scanning of said particulate, (d) and wherein said surface consists of a substance selected from the group consisting of beryllium or carbon with or without a sticky coating applied on the surface for enhanced particle adhesion, and the holder has a body consisting of an electrically conductive metal or metal alloy.

10. The apparatus of claim 9 wherein said holder body includes a stem, and a flange on the stem for mounting said surface, said surface defined by a substrate of said substance.

11. In apparatus enabling gas entrained particulate collection and transfer of collected particulate into position for analysis by a scanning electron microscope, the improvement comprising (a) structure forming a cavity and including a nozzle having an orifice for directing flow of said gas and particulates entrained therein toward the cavity, (b) and a holder mounted in the cavity in association with said structure and having an electrically conductive surface facing toward said orifice in the path of flow and normal to the path of flow from the orifice so that particulates collect on the holder proximate said surface, (c) the holder sized and adapted for use in the scanning electron microscope whereby the holder may be directly transferred to said microscope for electron beam scanning of said particulate, (d) a bracket mounting said holder, the bracket located in said cavity and removably attached to said structure which is cup-shaped, and, (e) wherein said holder is positioned by the bracket so that at least one portion of said surface is retained in engagement with the nozzle, whereby said surface is accurately positioned relative to said orifice.

12. The apparatus of claim 11 wherein at least two spaced portions of said surface are retained in engagement with the nozzle, the surface extent between said spaced portions being in alignment with said orifice to collect said particulates.

13. The apparatus of claim 12 wherein the nozzle has at least two lands engaging said surface.

14. The apparatus of claim 13 wherein there are radial channels in said lands so that up to four land feet are defined to engage said surface.

15. The apparatus of claim 12 wherein the bracket includes a cross-piece mounting the holder, and fasteners carried by the cross-piece at generally opposite sides of the holder for removable attachment to said structure.

16. For use in apparatus enabling gas entrained particulate collection and transfer of collected particulates into position for scanning by the electron beam of a scanning electron microscope, said apparatus also including cup-shaped structure forming a cavity and including a nozzle having at least one orifice of cross dimension less than about 0.1 inch for directing flow of said gas and particulates entrained therein toward the cavity, the improvement comprising (a) a holder to be mounted in the cavity in association with said structure and having an electrically conductive surface sized to face toward said orifice in the path of flow from the orifice so that particulates collect on the holder proximate said surface, (b) the holder sized for use in the scanning electron microscope whereby the holder may be directly transferred to said microscope for electron beam scanning of said particulate, (c) the holder surface consisting of a low molecular weight substance, and the holder having a body consisting of electrically conductive metal or metal alloy.

17. The apparatus of claim 16 including a bracket including a cross-piece mounting the holder and sized for reception in the cavity and attachment to said structure with the holder surface directly facing the orifice in predetermined spaced relation thereto.

18. For use in apparatus enabling gas entrained particulate collection and transfer of collected particulates into position for scanning by the electron beam of a scanning electron microscope, said apparatus also including cup-shaped structure forming a cavity and including a nozzle having at least one orifice for directing flow of said gas and particulates entrained therein toward the cavity, the improvement comprising (a) a holder to be mounted in the cavity in association with said structure and having an electrically conductive surface sized to face toward said orifice in the path of flow from the orifice so that particulates collect on the holder proximate said surface, (b) the holder sized for use in the scanning electron microscope whereby the holder may be directly transferred to said microscope for electron beam scanning of said particulate (c) and wherein said surface consists of a substance selected from the group consisting of beryllium and carbon, and the holder has a body consisting of an electrically conductive metal or metal alloy, or of the same material as said surface.

19. The apparatus of claim 18 wherein said holder body includes a stem, and a flange on the stem and mounting said surface, said surface defined by a substrate of said substance.

20. For use in apparatus enabling gas entrained particulate collection and transfer of collected particulates into position for scanning by the electron beam of a scanning electron microscope, said apparatus also including cup-shaped structure forming a cavity and including a nozzle having at least one orifice for directing flow of said gas and particulates entrained therein toward the cavity, the improvement comprising
  (a) a holder to be mounted in the cavity in association with said structure and having an electrically conductive surface sized to face toward said orifice in the path of flow from the orifice so that particulates collect on the holder proximate said surface,
  (b) the holder sized for use in the scanning electron microscope whereby the holder may be directly transferred to said microscope for electron beam scanning of said particulate,
  (c) and including a bracket having a cross-piece mounting the holder and sized for reception in the cavity and attachment to said structure with the holder surface directly facing the orifice in predetermined spaced relation thereto,
  (d) and wherein the bracket includes fasteners carried by the cross-piece at generally opposite sides of the holder, for removable attachment to said structure, and spring means urging the bracket toward the nozzle.

21. The method of using apparatus enabling gas entrained particulate collection and transfer of collected particulate into position for analysis by a scanning electron microscope, the apparatus comprising
  (a) structure forming a cavity and including a nozzle having an orifice for directing flow of said gas and particulates entrained therein toward the cavity,
  (b) and a holder mounted in the cavity in association with said structure and having an electrically conductive surface facing toward said orifice in the path of flow and normal to the path of flow from the orifice so that particulates collect on the holder proximate said surface,
  (c) the holder sized and adapted for use in the scanning electron microscope whereby the holder may be directly transferred to said microscope for electron beam scanning of said particulate, which includes the steps:
    (i) flowing said gas and entrained particulates through said nozzle and toward said holder surface, to cause particulate collection on said surface,
    (ii) then demounting said holder from said structure and directly transferring the holder to a scanning electron microscope, and
    (iii) operating the electron microscope to scan the particulates on the holder surface as they were collected.

* * * * *